(12) United States Patent
Chen et al.

(10) Patent No.: US 9,023,886 B2
(45) Date of Patent: May 5, 2015

(54) NANOSUSPENSION OF A POORLY SOLUBLE DRUG VIA MICROFLUIDIZATION PROCESS

(75) Inventors: Ming J. Chen, West Windsor, NJ (US); Ho-Wah Hui, Somerset County, NJ (US); Thomas Lee, Bedminster, NJ (US); Paul Kurtulik, Somerset, NJ (US); Sekhar Surapaneni, Somerset, NJ (US)

(73) Assignee: Celgene Corporation, Summit, NJ (US)

( * ) Notice: Subject to any disclaimer, the term of this patent is extended or adjusted under 35 U.S.C. 154(b) by 326 days.

(21) Appl. No.: 12/942,930

(22) Filed: Nov. 9, 2010

(65) Prior Publication Data

US 2011/0124702 A1    May 26, 2011

Related U.S. Application Data

(60) Provisional application No. 61/259,903, filed on Nov. 10, 2009.

(51) Int. Cl.
| | |
|---|---|
| *A61K 31/4035* | (2006.01) |
| *A61K 9/10* | (2006.01) |
| *A61K 31/4045* | (2006.01) |
| *A61K 47/38* | (2006.01) |

(52) U.S. Cl.
CPC ............. *A61K 9/10* (2013.01); *A61K 31/4045* (2013.01); *A61K 47/38* (2013.01); *Y10S 977/906* (2013.01); *Y10S 977/773* (2013.01)

(58) Field of Classification Search
CPC ...... A61K 9/10; A61K 47/38; A61K 31/4045
USPC ............................ 977/906, 773; 514/416, 417
See application file for complete search history.

(56) References Cited

U.S. PATENT DOCUMENTS

| 5,091,187 | A | 2/1992 | Haynes | |
|---|---|---|---|---|
| 6,018,080 | A | 1/2000 | Dearn | |
| 6,068,858 | A | 5/2000 | Liversidge et al. | |
| 6,579,895 | B2 * | 6/2003 | Karim et al. | 514/406 |
| 2002/0012704 | A1 * | 1/2002 | Pace et al. | 424/489 |
| 2005/0239867 | A1 | 10/2005 | Zeldis | |
| 2006/0183787 | A1 | 8/2006 | Muller et al. | |
| 2008/0145430 | A1 | 6/2008 | Panmai et al. | |
| 2010/0266692 | A1 | 10/2010 | Bloom et al. | |
| 2010/0330156 | A1 | 12/2010 | Liu et al. | |

FOREIGN PATENT DOCUMENTS

| WO | WO 03/080049 | * 10/2003 | ......... A61K 31/4035 |
|---|---|---|---|
| WO | WO 2006/062875 | 6/2006 | |
| WO | WO 2009/010837 | 1/2009 | |
| WO | WO 2009/042114 | 4/2009 | |

OTHER PUBLICATIONS

Bottomley, *Drug Delivery Report*, 2006:20-21.
Jinno et al, *J. Cont. Rel.* 2006, 206(111):56-64.
Liversidge et al., *Int. J. Pharm.* 1995, 125:91-97.
Merisko-Liversidge et al., *Eur.J.Pharm. Sci.* 18:113-20, 2003.
Merisko-Liversidge et al., *Toxicology Pathology* 2008, 36:43-48.
Muller, *Adv. Drug Delivery Rev.* 2001, 47:3-19.
Pace et al., *Pharm. Tech*, 1999, 23:116-134.
Panagiotou et al., *Nanotech.* 2007, 4:246-249.
Panagiotou et al., *Chemical Engineering Progress* 2008:33-39.
Pathak et al. *Expert Opin. Drug Deliv.* 2005(2):747-761.
Rabinow, *Nature Reviews: Drug Delivery* 2004, 3:785-796.

\* cited by examiner

*Primary Examiner* — Sean Basquill
(74) *Attorney, Agent, or Firm* — Jones Day

(57) ABSTRACT

Provided are compositions and methods for preparation and administration of an oral nanosuspension of a poorly soluble drug with improved bioavailability. The method is optimized through microfluidization process with water soluble polymeric excipients in the absence of surfactants.

10 Claims, 6 Drawing Sheets

NANOSUSPENSION OF A POORLY SOLUBLE DRUG VIA MICROFLUIDIZATION PROCESS

This application claims priority to U.S. Provisional Application No. 61/259,903 filed Nov. 10, 2009, which is incorporated herein by reference in its entirety.

FIELD

Provided herein are nanosuspension compositions of poorly soluble drugs with improved bioavailability and methods of preparation of such compositions.

BACKGROUND

Many new chemical entities are too potent, too toxic, or too water-insoluble, making them undesirable development candidates. Potency and toxicity are intrinsic to molecular design and are typically best remedied by altering or refining chemical structure. On the other hand, poor solubility typically leads to poor oral bioavailability, fed/fasted variations in bioavailability, cumbersome and inconvenient dosage forms, and may necessitate the use of harsh solubilizing agents that are associated with adverse side effects. A new generation of nanoparticulate drug delivery systems specifically designed for resolving formulation issues associated with these poorly water-soluble compounds could be solving the problem (see, e.g., Liversidge G, Cundy K. "Particle size reduction for improvement of oral bioavailability of hydrophobic drugs: I. Absolute oral bioavailability of nanocrystalline danazol in beagle dogs", *Int. J. Pharm.* 1995, 125:91-97).

Nanoparticles, in comparison to micronized drug particles, have significantly greater surface area. The increase in surface area enhances dissolution rate, thereby improving delivery efficiency for the most commonly-used routes of administration (Jinno J, et al. "Effect of particle size reduction on dissolution and oral absorption of a poorly water-soluble drug, cilostazol, in beagle dogs", *J. Cont. Rel.* 2006, 206 (111): 56-64).

A number of methods are available to produce drug nanoparticles, involving either top-down processes, based upon attrition, or bottom-up processes, based upon molecular deposition. Examples of the latter include spray freezing into liquid (SFL), rapid expansion from a liquefied-gas solution (RESS), and gas antisolvent recrystallization (GAS). RESS and GAS represent two approaches in development based upon supercritical fluid technology (Pathak P, Meziani M J, Sun Y-P., "Supercritical fluid technology for enhanced drug delivery", *Expert Opin. Drug Deliv.* 2005(2):747-761). RESS is used for compounds that are soluble in supercritical fluids. The resulting solution is subjected to a rapid reduction in pressure and/or a rapid elevation in temperature, causing the solute to emerge from solution. Under optimal conditions, submicron particles can be generated. The GAS process is used for compounds that are not soluble in supercritical fluids. The compound is first dissolved in an organic solvent and then re-crystallized by admixing with the supercritical fluid. More recently, Microfluidics (Newtown, Mass.) has employed impinging-jet crystallization technology to produce crystalline nanoparticles (Panagiotou T, Fisher R J. "Form Nanoparticles via Controlled Crystallization", *Chemical Engineering Progress* 2008:33-39).

The alternate path for generating drug nanoparticles entails top-down processes. Large drug crystals (typically >5 microns in diameter) are subjected either to high-pressure homogenization or high-energy wet milling in a fluid phase consisting essentially of water, yielding drug particles in the nanometer size range (Merisko-Liversidge E, Liversidge G G, Cooper E R. "Nanosizing: a formulation approach for poorly-water-soluble compounds", *Eur. J. Pharm. Sci.* 2004, 18:113-20).

A key to the success of both processes is the inclusion of surface modifiers in the fluid phase. The surface modifiers prevent aggregation and/or Ostwald ripening of the nanoparticles during and after processing. Surface modifiers are chosen from the list of pharmaceutically-acceptable substances and typically possess surface active properties capable of wetting the large drug crystals and providing steric and/or ionic stabilization to the resulting nanometer-size drug particles. Some of the most commonly-used stabilizers include povidones, phospholipids, polysorbates, poloxamers, cellulosics, and anionic surfactants, e.g. SLS and DOSS.

Microfluidizer technology is based on the use of the microfluidizer, which is a jet stream homogenizer of two fluid streams collied frontally with high velocity (up to 100 m/sec) under pressures of up to 4000 bar. Turbulent flow and high shear forces cause particles collision, leading to particle diminution to the nanometer range. The high pressure applied and the high streaming velocity of the lipid can also lead to cavitation, additionally contributing to size diminution. To preserve the particles size, stabilization with phospholipids or other surfactants and stabilizers is required. A major disadvantage of this process is the required production time. In many cases, 50 to 100-time consuming passes are necessary for a sufficient particle size reduction (U.S. Pat. Nos. 6,018, 080 and 5,091,187). The high-pressure homogenization/microfluidization approach has been investigated over the years (Muller R. H., "Nanosuspensions as particulate drug formulations in therapy: rationale for development and what we can expect in the future", *Adv. Drug Delivery Rev.* 2001, 47:3-19; Rabinow B. E., "Nanosuspensions in drug delivery", *Nature Reviews: Drug Delivery* 2004, 3:785-796; Pace S. et al., "Novel injectable formulations of insoluble drugs", *Pharm. Tech,* 1999, 23:116-134; and Panagiotou T. et al., "Production of stable nanosuspensions using mircofluidics reaction technology", *Nanotech.* 2007, 4:246-249). High-energy wet milling process is also known (Bottomley K, "NanoTechnology for Drug Delivery: a Validated Technology?", *Drug Delivery Report,* 2006:20-21).

There are advantages and disadvantages to each approach. Published particle size data for homogenization processes indicate that this approach typically produces a dispersion with slightly broader particle size distribution relative to what has been achievable using the wet milling approach (Shah J, Wisniecki P, Wagner D, Shah P. "Case study: development of parenteral nanosuspensions: stability, manufacture and performance". At 42nd Annual Technology Arden Conference: Best Practices for Parenteral Dosage Forms: Formulation, Process, Development, Package Selection and Manufacturing. AAPS Meetings and Expositions, West Point, N.Y. 2007.) Also, high-energy wet milling typically uses a proprietary milling media in which contact points between the media and the drug particles bring about particle size reduction. The media used in Elan's NanoCrystal technology approach, for example, comprises highly cross-linked polystyrene spheres that have been engineered to withstand high shear forces, thereby minimizing concerns about media wear during manufacturing (Merisko-Liversidge E, Liversidge G G, "Drug Nanoparticles: Formulating Poorly Water-Soluble Compounds", *Toxicology Pathology* 2008, 36:43-48). The result is a population of drug nanoparticles characterized by high purity and a tight, reproducible particle-size distribution profile.

Formulating poorly water-soluble molecules using the various nano-sizing approaches adds tremendous value throughout the drug development cycle. NanoCrystal formulations can be prepared with as a little as 10 mg of active ingredient, and are often times used as clips to identify the optimal development candidate based on bioavailability and efficacy (U.S. Pat. No. 5,091,187). These formulations can be dosed via multiple routes of administration, and since the formulations are well-tolerated and provide maximal exposure for a poorly water-soluble compound, they are an invaluable tool for toxicokinetic studies and target product profile.

A major challenge in realizing the full commercial potential of nanosizing is the successful conversion of stable drug nanoparticles into acceptable dosage forms. Furthermore, while microfluidization process has been used in connection with injectable formulations, the use of that process is much less common in connection with oral formulations. Regardless of the success in development of nanosizing technologies, the existing drawbacks trigger a need for more sofisticated procedures to obtain oral nanosuspensions of poorly soluble drugs with improved bioavailability.

SUMMARY

In one embodiment, provided is a method of preparation of an oral nanosuspension of a poorly soluble drug with improved bioavailability using a microfluidization process. In certain embodiment, the method of preparation of an oral nanosuspension of a poorly soluble drug comprises a step of stirring the drug, which has been micronized, in an aqueous polymeric excipient solution for wetting and dispersing in the absence of surfactants, followed by a step of passing the resulting mixture through a high-shear microfluidizer processor.

In one embodiment, provided is a nanosuspension of a poorly soluble drug with improved bioavailability made using a microfluidization process in the absence of surfactants, wherein said nanosuspension is suitable for a long term storage. In certain embodiments, the oral nanosuspension is stable for at least 2 months at room temperature. In certain embodiments, the oral nanosuspension is stable for at least 6 months at 5° C.

In another embodiment, provided is a method of administration of an oral nanosuspension of a poorly soluble drug with improved bioavailability comprising the step of microfluidization of the nanosuspension of a poorly soluble drug in the absence of surfactants and the step of dilution of the nanosuspension immediately before the administration in the presence of surfactants. Examples of surfactans include, but are not limited to, vitamin E-TPGS, Labrasol and Tween 20. In a specific embodiment, the surfactants are ionic surfactants. In certain embodiments, ionic surfactants include, but are not limited to, Sodium Lauryl Sulfate (SLS), i.e., SDS.

In one embodiment, provided is a nanosuspension formulation of a poorly soluble drug with improved bioavailability.

In yet another embodiment, provided is a formulation of a poorly soluble drug comprising a deagglomerated and particle size controlled nanosuspension with improved bioavailability.

In a particular embodiment, an oral nanosuspension with improved bioavailability is a nanosuspension of cyclopropyl-N-{2-[(1S)-1-(3-ethoxy-4-methoxyphenyl)-2-(methylsulfonyl)ethyl]-3-oxoisoindoline-4-yl}carboxamide. In another particular embodiment, a novel oral nanosuspension with improved bioavailability is a nanosuspension of (+)-{2-[1-(3-ethoxy-4-methoxyphenyl)-2-methylsulfonylethyl]-4-acetylaminoisoindoline-1,3-dione}.

In another embodiment, provided are methods of treating, preventing or managing various disorders using the nanosuspension formulations of cyclopropyl-N-{2-[(1S)-1-(3-ethoxy-4-methoxyphenyl)-2-(methylsulfonyl)ethyl]-3-oxoisoindoline-4-yl}carboxamide or (+)-{2-[1-(3-ethoxy-4-methoxyphenyl)-2-methylsulfonylethyl]-4-acetylaminoisoindoline-1,3-dione}.

DETAILED DESCRIPTION

Drug Substances

Figure 1:
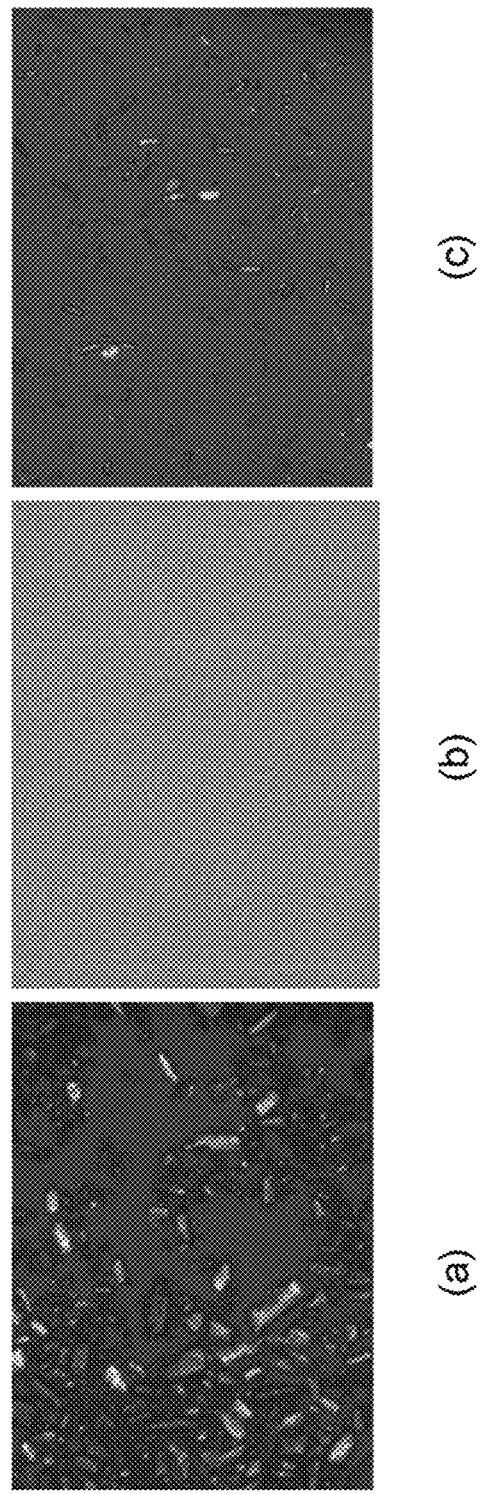
FIG. 1 depicts the images of micronized API (a) and nanosuspension A(b) before and after microfluidization process, and a suspension processed with solubilizers (c).

Poorly water soluble drugs often have limited exposure for toxicology and toxicokinetic studies and clinical trials. It was discovered that drug particles having a specific average particle size can be prepared by microfluidization process and that these particles are relatively stable. These particles are formulated into pharmaceutical compositions exhibiting improved bioavailability. The resulting pharmaceutical compositions can be used in toxicology formulations.

The methods and compositions provided herein can be practiced with a wide variety of drug substances. The drug substance is typically poorly soluble and dispersible in at least one liquid medium. In one embodiment, by "poorly soluble" it is meant that the drug substance has a solubility in the liquid dispersion medium of less than about 10 mg/ml. In another embodiment, "poorly soluble" means a solubility of less than 1 mg/ml. In yet another embodiment, "poorly soluble" means a solubility of less than 10 μg/ml.

The methods and compositions provided herein can be practiced with a liquid dispersion medium such as water and other liquid media in which a drug substance is poorly soluble and dispersible including, but is not limited to, aqueous salt solutions, sunflower oil and solvents. Solvents include, but are not limited to, ethanol, t-butanol, hexane and glycol. The pH of the aqueous dispersion media can be adjusted by techniques known to those skilled in the art.

Representative illustrative drug substances that can be used in the practice of the invention include, but are not limited to, cyclopropyl-N-{2-[1-(3-ethoxy-4-methoxyphenyl)-2-(methylsulfonyl)ethyl]-3-oxoisoindoline-4-yl}carboxamide having the following formula (I):

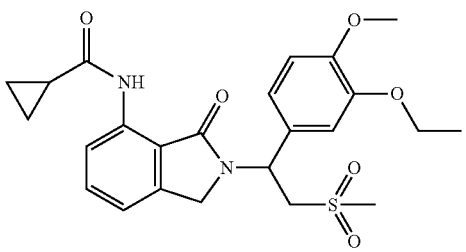 [SMILES: CCOc1cc(C(CS(C)(=O)=O)N2Cc3cccc(NC(=O)C4CC4)c3C2=O)ccc1OC]

or a pharmaceutically acceptable salt or stereoisomer thereof, and {2-[1-(3-ethoxy-4-methoxyphenyl)-2-methylsulfonylethyl]-4-acetylaminoisoindoline-1,3-dione} having the following formula (II):

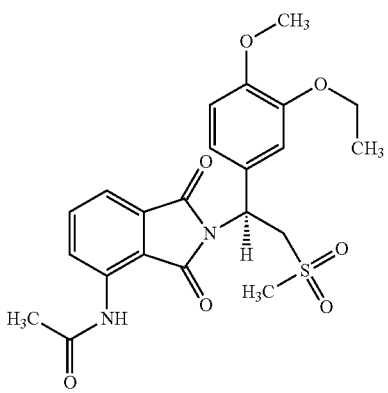 [SMILES: CCOc1cc([C@@H](CS(C)(=O)=O)N2C(=O)c3cccc(NC(C)=O)c3C2=O)ccc1OC]

or a pharmaceutically acceptable salt or stereoisomer thereof.

In one embodiment, the compound is cyclopropyl-N-{2-[(1S)-1-(3-ethoxy-4-methoxyphenyl)-2-(methylsulfonyl)ethyl]-3-oxoisoindoline-4-yl}carboxamide. In another embodiment, the compound is (+)-{2-[1-(3-ethoxy-4-methoxyphenyl)-2-methylsulfonylethyl]-4-acetylaminoisoindoline-1,3-dione}.

Microfluidizers and Microfluidization Process

Microfluidization may be conducted using any suitable microfluidizer. Examples of microfluidizers include, but are not limited to, M-110P family of microfluidizers (Microfluidics, MA, U.S.A.).

Microfluidization process provided herein comprises a step of processing of dispersion of a poorly soluble compound through the Microfluidizer processor. The process, and thus, the resulting particle size, is governed by a pressure applied and by a number of passes the compound goes through the Microfluidizer. When the applied pressure is relatively high, the number of passes can be lower and vise versa.

In one embodiment, provided is a method of preparation of an oral nanosuspension of a poorly soluble drug using a microfluidization process, wherein the pressure applied is in the range of 5-35K psi. In another embodiment, the applied pressure is in the range of 10-35K psi. In another embodiment, the applied pressure is in the range of 15-30K psi. In another embodiment, the applied pressure is in the range of 25-30K psi.

In one embodiment, provided is a method of preparation of an oral nanosuspension of a poorly soluble drug using a microfluidization process, wherein the number of passes is in the range of 10-200. In another embodiment, the number of passes is in the range of 20-200. In another embodiment, the number of passes is in the range of 30-200. In another embodiment, the number of passes is in the range of 40-200.

Method of Making of Nanosuspension of Poorly Water Soluble Drugs

In one embodiment, provided is a method of preparation of an oral nanosuspension of a poorly soluble drug using a microfluidization process without surfactants comprising a step of stirring the micronized compound in an aqueous polymeric excipient solution for wetting and solubilization, followed by a step of passing through a high-shear microfluidizer processor (Microfluidics, MA, USA; Model M 110P). The suitable excipients include, but are not limted to, PVP, CMC, HPMC, PEG, PEO, transcutol and glycerin.

In one embodiment, the aqueous polymeric excipient is a low molecular weight polymeric excipient. As used herein, and unless otherwise specified, the term "low molecular polymeric excipient" refers to a polymeric excipient that provides an apparent viscosity of less than 2000 CPS when measured as a 2% by weight solution in water at 20° C. Alternatively, in certain embodiments, the term "low molecular weight polymeric excipient" may refer to a polymeric excipient whose molecular weight is less than 50,000.

In another embodiment, provided is an oral nanosuspension of a poorly soluble drug made using a microfluidization process without surfactants, wherein said nanosuspension is suitable for a long term storage. As used herein, "long term storage" is defined as the period of time during which a nanosuspension is stable, e.g., over 1 month, over 3 months, over 6 months, over 1 year, or over 2 years.

In one embodiment, the stability of a nanosuspension of a poorly soluble drug is defined by the time period during which over 70%, 80% or 90% of the API remains undegraded, assessed using any conventional method known in the art.

Provided is a nanosuspension of a poorly soluble drug using a microfluidization process wherein the resulting nanosuspension is stable for a long term storage at a low temperature (e.g., 5° C.) and a method of preparing the same. Also provided is a nanosuspension of a poorly soluble drug using a microfluidization process wherein the resulting nanosuspension is stable for a long term storage at a room temperature (22° C.) and a method of preparing the same.

In certain embodiments, provided is a method of preparation of a nanosuspension of a poorly soluble drug using a microfluidization process wherein the resulting nanosuspension is stable for more than 1, 5, 10, 15, 20 or 25 days at a low temperature (e.g., 5° C.). In certain embodiments, provided is a method of preparation of a nanosuspension of a poorly soluble drug using a microfluidization process wherein the resulting nanosuspension is stable for more than 1, 2, 3 or 4 weeks at a low temperature (e.g., 5° C.). In certain embodiments, provided is a method of preparation of a nanosuspension of a poorly soluble drug using a microfluidization process wherein the resulting nanosuspension is stable for more than 1, 3, 6, 12, 18 or 24 months at a low temperature (e.g., 5° C.).

In certain embodiments, provided is a method of preparation of a nanosuspension of a poorly soluble drug using a microfluidization process wherein the resulting nanosuspension is stable for more than 1, 5, 10, 15, 20 or 25 days at a room temperature (22° C.). In certain embodiments, provided is a method of preparation of a nanosuspension of a poorly soluble drug using a microfluidization process wherein the resulting nanosuspension is stable for more than 1, 2, 3 or 4 weeks at a room temperature (22° C.). In certain embodiments, provided is a method of preparation of a nanosuspension of a poorly soluble drug using a microfluidization process wherein the resulting nanosuspension is stable for more than 1, 3, 6, 12, 18 or 24 months at a room temperature (22° C.).

The particle size distribution of the resultant suspensions can be measured using any instrumentation. An example is laser diffraction using a Cilas Particle Size Analyser 1190. The images of the particles can be taken using, for example, the microscope "Olympus". The resolution rates can be determined, for example, by a PION μDISS Profiler.

In one embodiment, the oral nanosuspension is a nanosuspension of cyclopropyl-N-{2-[(1S)-1-(3-ethoxy-4-methoxyphenyl)-2-(methylsulfonyl)ethyl]-3-oxoisoindoline-4-yl}carboxamide. In another embodiment, the nanosuspension is a nanosuspension of (+)-{2-[1-(3-ethoxy-4-methoxyphenyl)-2-methylsulfonylethyl]-4-acetylaminoisoindoline-1,3-dione}.

In processing dispersions of poorly soluble compounds by microfluidization, the concentration of the polymer excipients should be adequately adjusted to avoid plugging of microfluidizer process. In addition, excipients with higher molecular weight typically result in particles with larger size compared to the lower molecular weight excipients due, in part, to the fact that higher shield force is necessary for higher molecular weight compounds. Thus, the appropriate molecular weight of the excipients should be determined according to the desired particle size. In general, solvent incorporations have less impact on particle size increase.

In certain cases, agglomeration of microfluidized paprticles may occur. In this regard, proper dispersants may be employed to minimize agglomeration, alone or in combination with surfactants. Such dispersants and/or surfactants are typically added when the microfluidized solution is diluted for administration. In certain embodiments, co-solvents may be employed for solubilization of aggregated particles. Suitable co-solvents include, but are not limited to, transcutol, PEG 300-8000, glycerol, and ethanol. Surfactants are described in more detail herein elsewhere.

Accordingly, also provided is a method of making a nanosuspension of a poorly soluble drug comprising the first phase which is a process of fluidization of a specific formulation that leads to a stable concentrated nanosuspension; and the second phase which is a process of dilution of the concentrated nanosuspension in the presence of dispersants, co-solvents and/or surfactants which leads to formation of deagglomerated and particle size controlled nanoparticles with enhanced bioavailability.

Surfactants for Poorly Water Soluble Drugs

In one embodiment, nanosuspension formulation made using microfluidization process is diluted immediately before its administration. In another embodiment, the diluted solution comprises one or more surfactants.

Surfactants are wetting agents that lower the surface tension of a liquid allowing easier spreading and lower the interfacial tension between two liquids. Surfactants are usually organic compounds that are amphiphilic, therefore, they are soluble in both organic solvents and water. Surfactants reduce the surface tension of water by adsorbing at the liquid-gas interface. They also reduce the interfacial tension between oil and water by adsorbing at the liquid-liquid interface.

Surfactants are classified into two primary groups: ionic (anionic, cationic and zwitterionic) (dual charge) and non-ionic.

The examples of non-ionic surfactants include, but are limited to, alkyl poly(ethylene oxide), copolymers of poly(ethylene oxide) and poly(propylene oxide), alkyl polyglucosides, such as octyl glucoside, decyl maltoside, fatty alcohols, cetyl alcohol, oleyl alcohol, cocamide MEA, cocamide DEA, polysorbates, such as Tween 20, Tween 80, and dodecyl dimethylamine oxide.

The examples of ionic surfactants include, but are limited to, rerfluorooetanoate (PFOA or PFO), perfluorooctanesulfonate (PFOS), sodium dodecyl sulfate (SDS), ammonium lauryl sulfate, sodium lauryl ether sulfate (SLES), alkyl benzene sulfonate, soaps, or a fatty acid salts (anionic), cetyl trimethylammonium bromide (CTAB) a.k.a. hexadecyl trimethyl ammonium bromide, and other alkyltrimethylammonium salts, cetylpyridinium chloride (CPC), Polyethoxylated tallow amine (POEA), Benzalkonium chloride (BAC), benzethonium chloride (BZT) (cationic), dodecyl betaine, cocamidopropyl betaine and coco ampho glycinate (zwitterionic).

In one embodiment, the surfactant is a non-ionic surfactant. In another embodiment, the non-ionic surfactant is vitamin E-TPGS, Labrasol or Tween-20. In one embodiment, the surfactant is an ionic surfactant. In another embodiment, the ionic surfactant is SLS.

Method of Administration of Nanosuspension of Poorly Water Soluble Drugs

Provided is a method of administration of an oral nanosuspension of a poorly water soluble drug with improved bioavailability comprising a step of microfluidization of a nanosuspension in the absence of surfactants, a step of dilution of a nanosuspension immediately before the administration of a nanosuspension in the presence of surfactants, and a step of administering the diluted nanosuspension formulation to a subject.

As provided herein, "immediately before the administration" means that a nanosuspension is diluted in the period of time between about 2 min and about 10 hours, or between about 5 min and about 5 hours, or between about 30 min and about 4 hours before its administered to a subject.

In particular embodiments, the surfactants are non-ionic surfactants. In a specific embodiment, the non-ionic surfactants include, but are not limited to, vitamin E-TPGS, Labrasol and Tween-20. In one embodiment, the surfactant is an ionic surfactant. In another embodiment, the ionic surfactant is SLS.

To achieve an improved availability of a nanosuspension of a poorly water-soluble drug, a nanosuspension concentrate may be diluted before administration. In one embodiment, the dilution process comprises a dilution of a nanosuspension of a poorly soluble drug from a concentrate in the presence of an excipient and a surfactant. In a specific embodiment, the excipient is HPMC E5. In another specific embodiment, the surfactant is SLS. The amount of the excipient and surfactant can be varied according to the properties of the drug substance to be formulated, the desired particle size, and the particular type of excipient or surfactant. In certain embodiments, the amount of excipient can be 0.05%-20%. In certain embodiments, the amount of excipient can be 0.1%40%. In certain embodiments, the amount of excipient can be 0.2%-5%. In certain embodiments where a non-ionic surfactant is employed, the amount of surfactant can be 0.1%-25%, 0.5%-15% or 1%-10%. In certain embodiments where an ionic surfactant is employed, the amount of surfactant can be 0.02%-10%, 0.1%-8% or 0.5%-5%.

It was discovered that the resulting nanosuspension has an increased solubility and bioavailability. In some embodiments, the solubility of the nanosuspension increases 40 folds over 40 minutes. It was also discovered that, using the methods provided herein, the nanoparticles deagglomerate and swell up to reach the proper mean diameter.

In some embodiments, the concentrated nanosuspension and diluent (e.g., surfactant) are not mixed prior to administration, but the concentrated nanosuspension and diluent are sequentially administered, causing the two mixed in situ. Accordingly, also provided herein is a method for administering an oral nanosuspension of a poorly water soluble drug comprising the steps of: (1) administering a concentrated nanosuspension made using methods provided herein; (2) administering a diluent comprising a surfactant, whereby the concentrated nanosuspension and diluent are mixed in situ.

In some embodiments, stable nanosupensions of a poorly soluble drug are achieved by stabilizers without recrystallization. Optimal process pressure and time may be determined to obtain optiman particle size. In some embodiments, the solubility can be enhanced by reformulating the microfluidization-processed nanosuspensions with surfactants while slightly increasing the particle size. Increase in processing pressure and processing time may result in further reduction of particle size. In some embodiments, the optimal process is obtained in the absence of surfactants. The solubility of the suspension can be further enhanced by adding surfactants to the nanosuspension after microfluidization process.

Methods of Treatment, Prevention and Management of a Disease Using a Nanosuspension of a Poorly Soluble Drug The formulations comprising cyclopropyl-N-{2-[(1S)-1-(3-ethoxy-4-methoxyphenyl)-2-(methylsulfonyl)ethyl]-3-oxoisoindoline-4-yl}carboxamide or (+)-{2-[1-(3-ethoxy-4-methoxyphenyl)-2-methylsulfonylethyl]-4-acetylaminoisoindoline-1,3-dione} or a pharmaceutically acceptable salt, solvate, hydrate, or clathrate thereof provided herein can be used to treat, prevent and/or manage various disorders including, but are not limited to, heart disease, such as congestive heart failure, cardiomyopathy, pulmonary edema, endotoxin-mediated septic shock, acute viral myocarditis, cardiac allografic rejection, and myocardial infarction; solid tumors, including but not limited to, sarcoma, carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular cancer, lung carcinoma, small cell lung carcinoma, bladder carcinoma, epithelial carcinoma, glioma, astrocytoma, medulloblastoma, craniopharyngioma, ependymnoma, Kaposi's sarcoma, pinealoma, hemangioblastoma, acoustic neuroma, oligodendroglioma, menangioma, melanoma, neuroblastoma, and retinoblastoma; blood-born tumors including, but not limited to, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, chronic lymphocytic leukemia, hairy cell leukemia, multiple myeloma, acute and chronic leukemia, including lymphoblastic, myelogenous, lymphocytic, and myelocytic leukemia; asthma; inflammation; chronic or acute obstructive pulmonary disease; chronic or acute pulmonary inflammatory disease; Pruigo Nordularis, cutaneous lupus; dermatomyositis; sarcoidosis, including chronic cutaneous sarcoidosis; pain; rheumatoid arthritis; acute gouty arthritis; uveitis; rosacea, ankylosing spondylitis, psoriasis; psoriatic arthritis; Lichen Planus; atopic dermatitis; contact dermatitis; osteoarthritis; acne; inflammatory bowel disease; Crohn's Disease; Bechet's Disease; colitis; ulcerative colitis; arthritis or inflammation due to reperfusion.

In one embodiment, the disorder is psoriasis. In another embodiment, the disorder is psoriatic arthritis.

In another embodiment, the disorder is sarcoidosis. In another embodiment, the disorder is chronic cutaneous sarcoidosis.

In another embodiment, the disorder is cutaneous lupus.

The magnitude of a prophylactic or therapeutic dose of a nanosuspension of a poorly soluble drug in the acute or chronic management of a disease or condition varies with the nature and severity of the disease or condition. The dose, and perhaps the dose frequency, also varies according to the age, body weight, and response of the individual patient. Suitable dosing regimens can be readily selected by those skilled in the art with due consideration of such factors.

In one embodiment, the recommended daily dose range for the conditions described herein lies within the range of from about 1 mg to about 1000 mg per day, given as a single once-a-day dose, or as divided doses throughout a day. In another embodiment, the daily dose is administered twice daily in equally divided doses. In certain embodiments, a daily dose ranges from about 5 mg to about 500 mg. In certain embodiments, a daily dose ranges from between about 10 mg and about 250 mg. In one embodiment, the daily dose is administered as 5 mg, 10 mg, 15 mg, 20 mg, 25 mg, 50 mg, 100 mg, 150 mg, 200 mg, 250 mg, 300 mg, 350 mg, 400 mg, 450 mg or 500 mg dosage form.

In one embodiment, in managing a patient, the therapy should be initiated at a lower dose, for example, at about 1 mg to about 25 mg and increased if necessary, for example, up to about 200 mg to about 1000 mg per day as either a single dose or divided doses, depending on the patient's global response. In another embodiment, the daily dose, for example, is about 250 mg/kg.

Different therapeutically effective amounts may be applicable for different diseases and conditions, as will be readily known by those of ordinary skill in the art.

The invention is further described by the following non-limiting examples.

EXAMPLES

Example 1

Microfluidization Process of a Poorly Soluble Drug

An aqueous dispersion of cyclopropyl-N-{2-[(1S)-1-(3-ethoxy-4-methoxyphenyl)-2-(methylsulfonyl)ethyl]-3-oxoisoindoline-4-yl}carboxamide up to 200 mg/ml in 0.5% HPMC E5 were able to be processed through the Microfluidizer processor. A low concentration of polymer excipients (0.2% HPMC E5) caused the insufficient wetting of cyclopropyl-N-{2-[(1S)-1-(3-ethoxy-4-methoxyphenyl)-2-(methylsulfonyl)ethyl]-3-oxoisoindoline-4-yl}carboxamide and resulted in plugging of the processor. By processing at 27K psi for 100 passes, the mean particle size by volume was reduced from 8.0 µm to 0.39 µm, while by processing at 15K psi, the mean size was 0.91 µm. The $D_{90}$ of particle size by number was 0.09 µm. It was noted that the use of excipients with higher molecular weight resulted in particles with larger size compared to the lower molecular weight excipients, while solvent incorporations have less impact on particle size increase.

It was observed that formulation with surfactants, such as vitamin E-TPGS, Tween 20, Labrasol or SLS, had resulted in supersaturation of cyclopropyl-N-{2-[(1S)-1-(3-ethoxy-4-methoxyphenyl)-2-(methylsulfonyl)ethyl]-3-oxoisoindoline-4-yl}carboxamide and its re-crystallization into inhabitant needles using the microfluidization process. The images of a nanosuspension without surfactants before and after microfluidizer process, and a suspension containing Tween 20 after the process are shown in FIG. 1. The 200 mg/ml nanosuspension A was physically stable at room temperature for at least 2 months and at 5° C. for at least 6 months.

It was demonstrated that stable nanosupensions of a poorly water soluble drug were achieved by using stabilizers without recrystallization. Optimal process pressure and time resulted in mean particle size of 0.05 μm. The optimal process was obtained in the absence of surfactants. The solubility of the suspension can be further enhanced by adding surfactants to the nanosuspension after the microfluidization process. The resulted nanosuspensions of cyclopropyl-N-{2-[(1S)-1-(3-ethoxy-4-methoxyphenyl)-2-(methylsulfonyl)ethyl]-3-oxoisoindoline-4-yl}carboxamide have shown an enhanced dissolution rate and bioavailability.

Example 2

Formulation of Nanosuspension of a Poorly Soluble Drug

Figure 2:
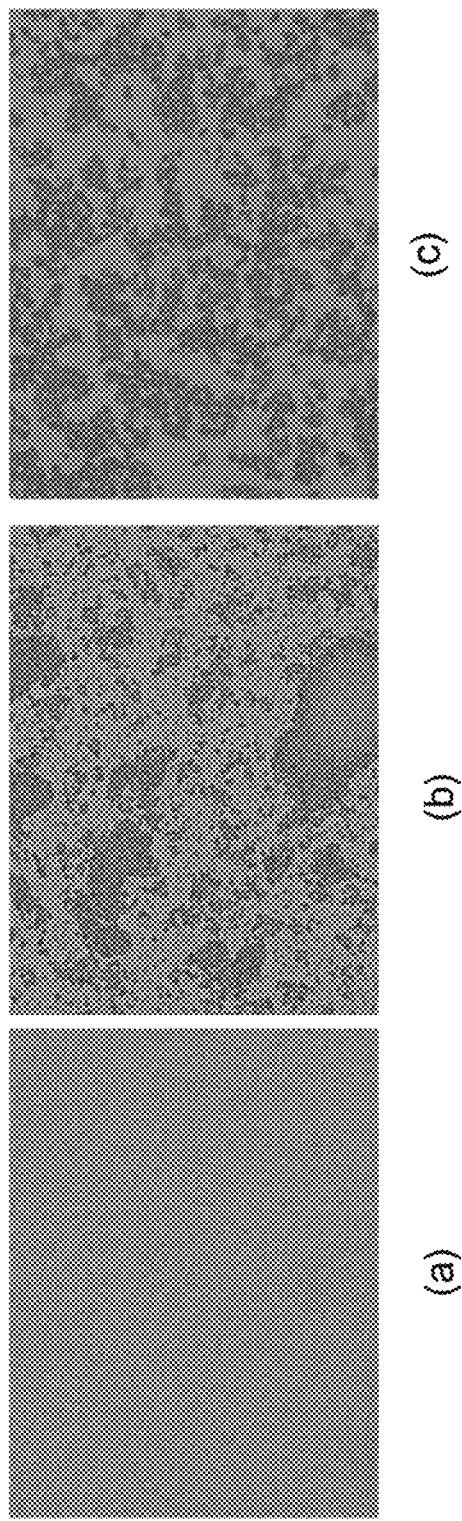
FIG. 2 depicts the images of agglomerated nanosuspension C (25 mg/ml) (b), which is diluted from nanosuspension A (a) and nanosuspension B (c).

When measuring the particle size of nanosuspension A, it was observed that it tends to agglomerate (FIG. 2). To obviate this problem, in further formulations dispersants were employed. Nanosuspensions B and C were eventually diluted to 25 mg/ml of cyclopropyl-N-{2-[(1S)-1-(3-ethoxy-4-methoxyphenyl)-2-(methylsulfonyl)ethyl]-3-oxoisoindoline-4-yl}carboxamide with 1.5% Labrasol and 1.5% Vitamin E-TPGS, but delivered differently. Nanosuspension B was the resulted admixture of A in 0.5% HPMC E5 and surfactants stirring at 300 rpm overnight, while nanosuspension C was administered in 0.5 HPMC E5 through oral gavage dose followed by rinsing the tube with 10 ml of the surfactants. Nanosuspension D is an admixture of nanosuspension A with 0.2% SLS stirred at room temperature for 30 minutes. Nanosuspension E is an admixture of nanosuspension A with different excipients.

Example 3

Dilution of Nanosuspension of a Poorly Soluble Drug

Upon dilution of nanosuspension A from 200 mg/ml to 25 mg/mL with 1.5% Labrasol and 1.5% Vitamin E TPGS, the solubility of the resulted nanosuspension B increased 40 folds over 40 minutes (FIG. 2). The images in FIG. 2 show that the nanoparticles deagglomerated while swelling up slightly to become 0.10 μm ($D_{90}$ by number). The mean size by volume increased from 0.39 μm. to 0.73 μm.

The dilution resulted in deagglomeration of nanoparticles of cyclopropyl-N-{2-[(1S)-1-(3-ethoxy-4-methoxyphenyl)-2-(methylsulfonyl)ethyl]-3-oxoisoindoline-4-yl}carboxamide with the following increase in bioavailability: 25 mg/ml nanosuspension diluted by 0.2% SLS and stirred for 30 minutes resulted in 147% improved relative explosure; 25 mg/ml nanosuspension diluted by 0.6 SLS and stirred for 60 minutes showed an enhanced dissolution rate; and 25 mg/ml nanosuspension diluted in 1.5% vitamin E-TPGS and 1.5% Labrasol resulted in 129% improved relative exposure (Table 1).

TABLE 1

The improvement of bioavailability by nanosuspensions determined by $C_{max}$, $T_{max}$ and $AUC_{0-24}$

| Formulation | Dose (mg/kg) | $C_{max}$ (ng/mL) | $T_{max}$ (hr) | $AUC_{0-24}$ (ng * h/mL) | Relative Exposure (percent) |
|---|---|---|---|---|---|
| Nano-suspension B | 250 mg/kg | 867.3 (164.5) | 8.0 (6.0-8.0) | 13690 (2142) | 107 |
| Nano-suspension C | 250 mg/kg | 1027 (209.2) | 8.0 (4.0-8.0) | 16490 (4117) | 129 |
| Nano-suspension D | 250 mg/kg | 1169 (98) | 2.0 (2.0-6.0) | 18793 (5641) | 147 |
| Control suspension E | 250 mg/kg | 765.5 (188.2) | 3.0 (2.0-10.0) | 12780 (4105) | 100 |

Example 4

Nanosuspension of Cyclopropyl-N-{2-[(1S)-1-(3-ethoxy-4-methoxyphenyl)-2-(methylsulfonyl)ethyl]-3-oxoisoindoline-4-yl}carboxamide obtained via Microfluidization Process Nanosuspensions were formed by initially stirring the micronized cyclopropyl-N-{2-[(1S)-1-(3-ethoxy-4-methoxyphenyl)-2-(methylsulfonyl)ethyl]-3-oxoisoindoline-4-yl}carboxamide in aqueous excipient solutions including PVP, CMC, HPMC, PEG, PEO, Transcutol, glycerin, and/or various surfactants for wetting and solubilization, followed by passing through a high-shear microfluidizer processor. The particle size distribution of the resultant suspensions was measured by a laser diffraction particle size analyzer. The images of the particles were taken using a microscope.

The images of formulations containing solubilizers, such as Vitamin E TPGS, Tween 20, or SLS, showed a supersaturation of cyclopropyl-N-{2-[(1S)-1-(3-ethoxy-4-methoxyphenyl)-2-(methylsulfonyl)ethyl]-3-oxoisoindoline-4-yl}carboxamide and recrystallization into inhabitant needles using microfluidization process. Aqueous dispersions of cyclopropyl-N-{2-[(1S)-1-(3-ethoxy-4-methoxyphenyl)-2-(methylsulfonyl)ethyl]-3-oxoisoindoline-4-yl}carboxamide up to 200 mg/ml in polymeric excipients were processed with this approach. The 200 mg/mL nanosuspension was physically stable at room temperature for 2 months, based on the images and particle size analysis. The $D_{90}$ of particle size by number was 0.09 μm. Processing the nanosuspension at 27K psi for 130 passes reduced mean particle size to 0.05 μm, while processing at 15K psi resulted in mean particle size of 0.08 μm. The use of excipients with higher molecular weight resulted in larger particles compared to the use of excipients with lower molecular weight, while solvent incorporations have less impact on particle size increase. At low concentration of polymer excipients, the wetting of 200 mg/ml cyclopropyl-N-{2-[(1S)-1-(3-ethoxy-4-methoxyphenyl)-2-(methylsulfonyl)ethyl]-3-oxoisoindoline-4-yl}carboxamide was insufficient, which resulted in plugging of the processor. Upon dilution from 200 mg/ml to 25 mg/ml with specific surfactants, the solubility increased 40 fold over 40 minutes. The images showed that the nanoparticles deagglomerate while swelling up slightly to become 0.10 μm ($D_{90}$).

Stable nanosuspensions of cyclopropyl-N-{2-[(1S)-1-(3-ethoxy-4-methoxyphenyl)-2-(methylsulfonyl)ethyl]-3-oxoisoindoline-4-yl}carboxamide were achieved by stabilizers without recrystallization. Optimal process pressure and time resulted in mean particle size of 0.05 µm. The solubility was enhanced by reformulating the microfluidization-processed nanosuspensions with surfactants while slightly increasing the particle size.

Example 5

Nanosuspension of (+)-{2-[1-(3-ethoxy-4-methoxyphenyl)-2-methylsulfonylethyl]-4-acetylaminoisoindoline-1,3-dione} Obtainable Via Microfluidization Process A nanosuspension of (+)-{2-[1-(3-ethoxy-4-methoxyphenyl)-2-methylsulfonylethyl]-4-acetylaminoisoindoline-1,3-dione} is formed by stirring the micronized compound in an aqueous excipient solution wherein the solution includes PVP, CMC, HPMC, PEG, PEO, Transcutol, or glycerin and/or surfactants such as Vitamin E-TPGS, Tween 20 or SLS, for wetting and solubilization, followed by the step of passing through a high-shear microfluidizer processor. The particle size distribution of the resultant suspensions is measured by a laser diffraction particle size analyzer. The images of the particles are taken using a microscope.

The 200 mg/ml nanosuspension of (+)-{2-[1-(3-ethoxy-4-methoxyphenyl)-2-methylsulfonylethyl]-4-acetylaminoisoindoline-1,3-dione} is physically stable at room temperature for 2 months, based on the images and particle size analysis. Processing the nanosuspension at 27K psi using 130 passes reduces mean particle size more significantly than the use of pressure of 15K psi. At a low concentration of polymer excipients, the wetting of 200 mg/ml of (+)-{2-[1-(3-ethoxy-4-methoxyphenyl)-2-methylsulfonylethyl]-4-acetylaminoisoindoline-1,3-dione} is insufficient. Upon dilution from 200 mg/ml to 25 mg/ml with specific surfactants, the solubility increases significantly.

Example 6

Figure 3:
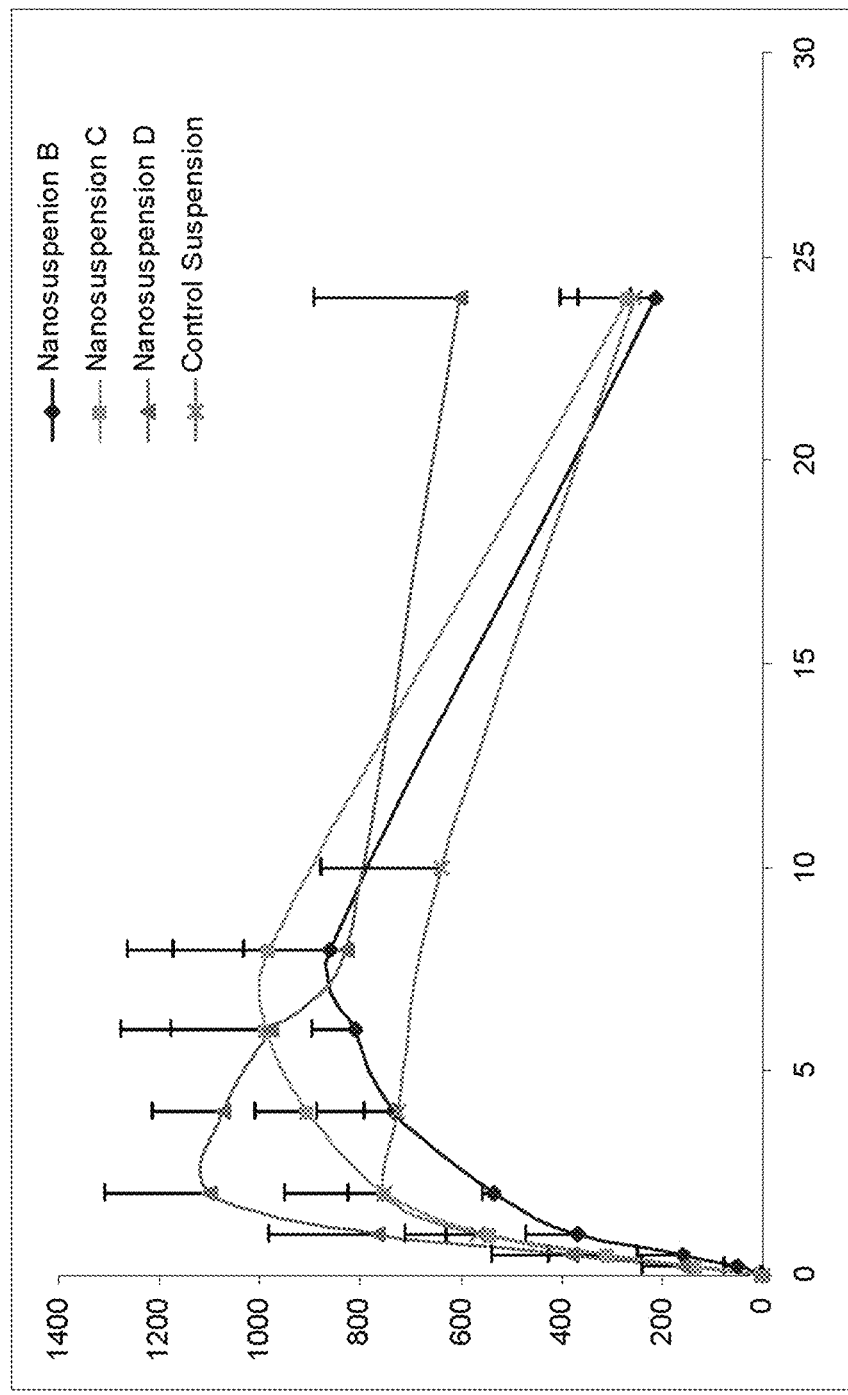
FIG. 3 demonstrates the mean plasma concentration-time profile of cyclopropyl-N-{2-[(1S)-1-(3-ethoxy-4-methoxyphenyl)-2-(methylsulfonyl)ethyl]-3-oxoisoindoline-4-yl}carboxamide with standard deviation.

Improvement of Bioavailability of a Poorly Soluble Drug Based on Pharmacokinetic Studies Pharmacokinetic evaluation of four formulations of cyclopropyl-N-{2-[(1S)-1-(3-ethoxy-4-methoxyphenyl)-2-(methylsulfonyl)ethyl]-3-oxoisoindoline-4-yl}carboxamide in male cynomolgus monkeys following oral administration was conducted. Oral gavage dosing formulations were continuously stirred throughout dosing. The gavage tube was rinsed with 10 ml of tap water or a surfactant solution following dosing. The individual and mean serum concentrations and pharmacokinetic parameters of nanosuspensions B, C and D versus a control micronized suspension E in 1% CMC are listed in Table 1. The absorption was fastest in nanosuspension D with a $T_{max}$ of 2 h. The $C_{max}$ and $AUC_{0-24hr}$ values for nanosuspension D were 1169 ng/ml and 18793 ng h/ml, respectively. The $AUC_{0-24hr}$ (12780 ng h/ml) of control suspension E was used as the reference for calculating the relative exposure. At the dose level of 250 mg/kg, the $AUC_{0-24hr}$ data show that the improvement of relative exposure by nanosuspensions B, C and D is 107%, 129% and 147%, respectively. The mean plasma concentration-time profile of cyclopropyl-N-{2-[(1S)-1-(3-ethoxy-4-methoxyphenyl)-2-(methylsulfonyl)ethyl]-3-oxoisoindoline-4-yl}carboxamide with standard deviation is depicted in FIG. 3.

Example 7

The Effect of Particle Size Reduction on Bioavailability

Although nanosuspensions B and C contained 25 mg/m of cyclopropyl-N-{2-[(1S)-1-(3-ethoxy-4-methoxyphenyl)-2-(methylsulfonyl)ethyl]-3-oxoisoindoline-4-yl}carboxamide with 1.5% Labrasol and 1.5% Vitamin E TPGS, nanosuspension B was allowed to disperse in surfactants overnight, while nanosuspension C was administered sequentially with the surfactants. It was observed that the particle size of nanosuspension C swelled up slightly overnight. The particle size reduction had a positive effect on bioavailability improvement. The $D_{50}$ of nanosuspension C analyzed by volume was 0.73 µm (by number −0.04 µm), while the $D_{50}$ of nanosuspension B was 0.46 µm (by number −0.04 µm). The $D_{50}$ of the original 200 mg/ml nanosuspension A was 0.39 µm (0.03 µm). Nanosuspension B with lower particle size resulted in more enhanced bioavailability than that of nanosuspension C.

Example 8

Dissolution Profile Comparison

Figure 4:
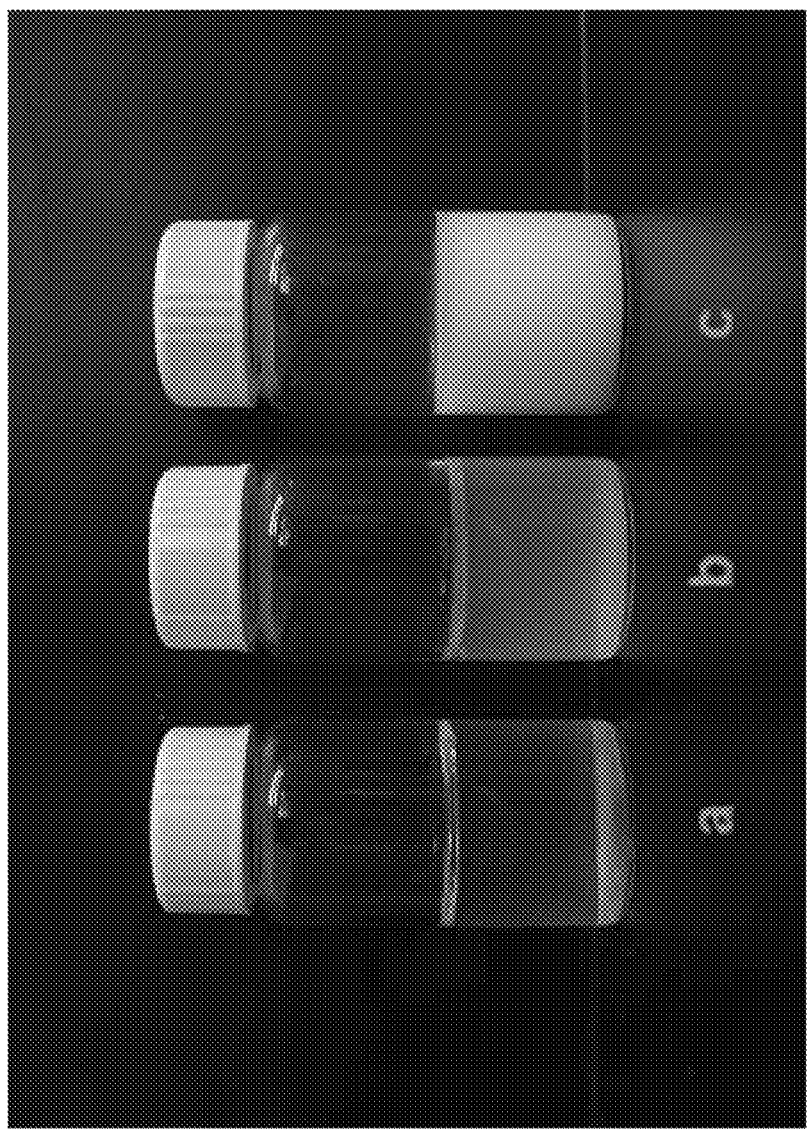
FIG. 4 depicts the appearance of milled API (a), micronized API (b) and nanosuspension F (c) prepared in the same vehicle.

Nanosuspension F was prepared by diluting a 200 mg/ml nanosuspension A with 0.6% SLS and stirring over 4 hours. The same conditions were applied to the same API quantity for micronized and milled materials. The appearance of nanosuspension F, micronized and milled API suspensions are shown in FIG. 4.

Figure 5:
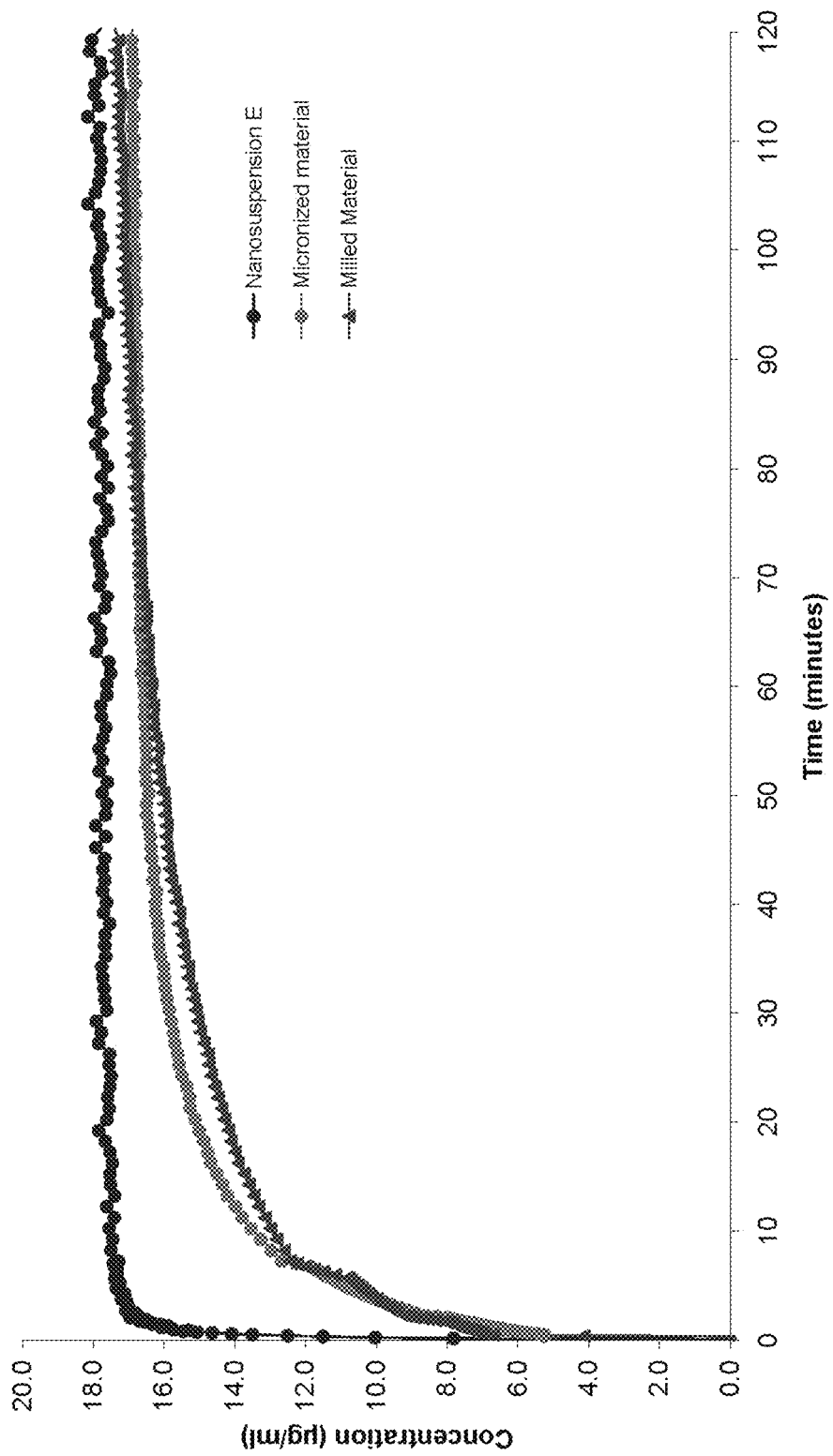
FIG. 5 depicts the dissolution profile of the nanosuspension F (a), micronized (b) and milled (c) cyclopropyl-N-{2-[(1S)-1-(3-ethoxy-4-methoxyphenyl)-2-(methylsulfonyl)ethyl]-3-oxoisoindoline-4-yl}carboxamide in 0.1% SLS vehicle.

An aliquot of the nanosuspension F, micronized and milled API suspensions were transferred into vessels containing 0.1% sodium lauryl sulfate. The dissolution profiles of these three suspensions were determined by a PionµDissolution. The results showed that the rate of dissolution ranked as follows: nanosuspension F>micronized API>milled API (FIG. 5).

Example 9

Deagglomeration of Nanoparticles of a Poorly Soluble Drug

Figure 6:
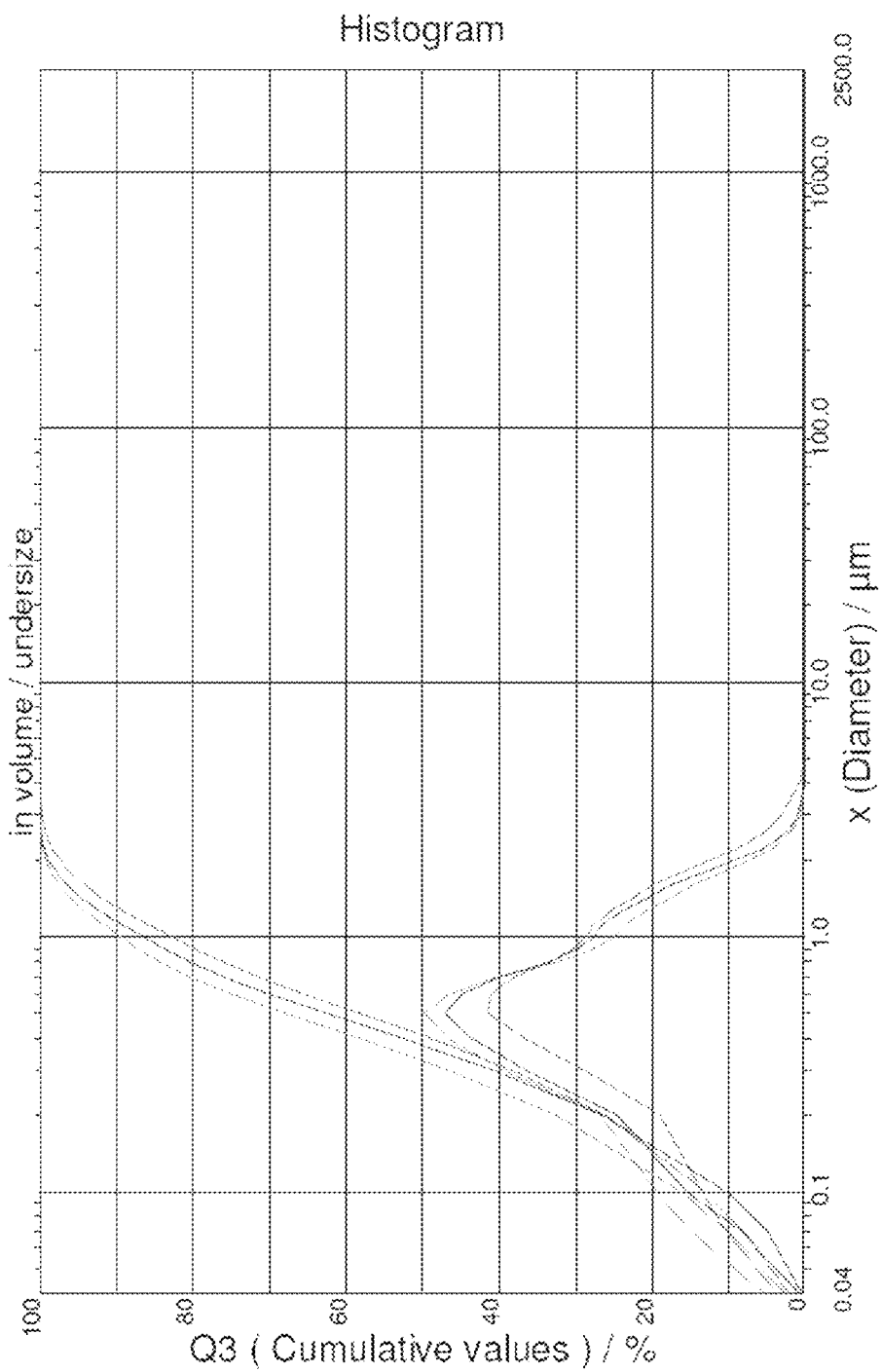
FIG. 6 depicts the overlay of particle size in volume/undersize of nanosuspensions at initial time (a), stirred in a vehicle for 30 minutes (b), and stirred in a vehicle for 120 minutes.

The particle size profiles in volume of original nanosuspension A, diluted to 25 mg/ml by 0.2% SLS and stirred at 300 rpm for 30 min and 120 min, were monitored by a Cilas particle size analyzer. The results are shown in FIG. 6. The overlay of the measurement indicates that deagglomeration of nanoparticles at 0.2% SLS concentration was optimized at the stirring for 30 minutes. This formulation condition is the actual nanosuspension D, which corresponds to the in vivo 147% improvement of relative exposure.

All publications, patent and patent applications cited in this specification are herein incorporated by reference as if each individual publication or patent application were specifically and individually indicated to be incorporated by reference. Although the foregoing invention has been described in some detail by way of illustration and examples for purposes of clarity and understanding, it will be readily apparent to those of ordinary skill in the art in light of the teachings of this invention that certain changes and modifications may be made thereto without departing from the spirit or scope of the appended claims.

What is claimed:

1. A method for preparing a nanosuspension of a poorly soluble drug with improved bioavailability, said method consists of:
   a) a first step consisting of microfluidizing a dispersion of a poorly soluble drug in an aqueous polymeric excipient solution in the absence of surfactants to form a stable concentrated nanosuspension; and
   b) a second step consisting of diluting the concentrated nanosuspension in the presence of dispersants, co-solvents or surfactants to form deagglomerated and particle size controlled nanoparticles.

2. The method of claim 1, wherein the poorly water soluble drug is cyclopropyl-N-{2-[(1S)-1-(3-ethoxy-4-methoxyphenyl)-2-(methylsulfonyl)ethyl]-3-oxoisoindoline-4-yl}carboxamide or (+)-{2-[1-(3-ethoxy-4-methoxyphenyl)-2-methylsulfonylethyl]-4-acetylaminoisoindoline-1,3-dione}.

3. The method of claim 1, wherein the nanosuspension is administered orally.

4. The method claim 1, wherein the aqueous polymeric excipient is a low molecular weight excipient.

5. The method of claim 4, wherein the low molecular weight excipient is HPMC E5.

6. The method of claim 1, wherein a co-solvent is selected from the group consisting of transcutol, PEG 300-800, glycerol, and ethanol.

7. The method of claim 1, wherein the surfactant is a non-ionic surfactant.

8. The method of claim 7, wherein the non-ionic surfactant is vitamin E-D-alpha tocopheryl polyethylene glycol 1000 succinate (E-TPGS), Labrasol™ or Tween-20™.

9. The method of claim 1, wherein the surfactant is a ionic surfactant.

10. The method of claim 9, wherein the ionic surfactant is sodium dodecyl sulfate (SLS).

\* \* \* \* \*